United States Patent [19]

Fauland et al.

[11] 4,016,262
[45] Apr. 5, 1977

[54] THERAPEUTIC COMPOSITIONS AND METHODS EMPLOYING N(6)-DISUBSTITUTED ADENOSINE COMPOUNDS

[75] Inventors: Erich Fauland, Mannheim-Gartenstadt; Wolfgang Kampe, Heddesheim, both of Germany; Kurt Stach, deceased, late of Mannheim-Waldhof, Germany; by Werner Plattner, executor, Linz, Austria; Harald Stork, Mannheim-Feudenheim; Karl Dietmann, Mannheim-Vogelstang, both of Germany

[73] Assignee: Boehringer Mannheim G.m.b.H., Mannheim-Waldhof, Germany

[22] Filed: May 30, 1975

[21] Appl. No.: 582,529

Related U.S. Application Data

[62] Division of Ser. No. 482,976, June 25, 1974, Pat. No. 3,929,764.

[30] Foreign Application Priority Data

Aug. 1, 1973 Germany ........................ 2338963

[52] U.S. Cl. .............................................. 424/180
[51] Int. Cl.² ........................................ A61K 31/70
[58] Field of Search ........................... 424/253, 180

[56] References Cited

UNITED STATES PATENTS

| | | | |
|---|---|---|---|
| 3,590,029 | 6/1971 | Koch et al. | 260/211.5 R |
| 3,706,728 | 12/1972 | Fauland et al. | 260/211.5 R |
| 3,840,521 | 10/1974 | Fauland et al. | 260/211.5 R |

*Primary Examiner*—Albert T. Meyers
*Assistant Examiner*—Daren M. Stephens
*Attorney, Agent, or Firm*—Burgess, Dinklage & Sprung

[57] ABSTRACT

N(6)-disubstituted adenosine compounds of the formula:

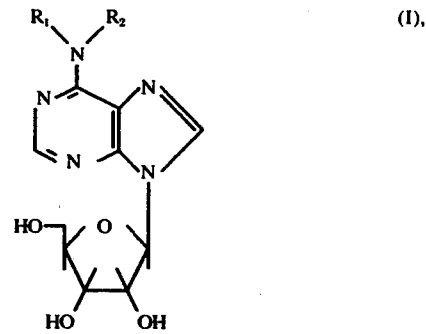

wherein
$R_1$ is alkenyl, cycloalkenyl or cycloalkenyl-alkyl; and
$R_2$ is alkenyl, cycloalkenyl, straight or branched-chain alkyl, cycloalkyl, bicycloalkyl, alkyl-cycloalkyl, or alkyl-bicycloalkyl;

and the pharmacologically compatible salts thereof; exhibit outstanding anti-lipolytic, anti-hyperlipaemic and anti-hypercholesterolaemic action.

30 Claims, No Drawings

THERAPEUTIC COMPOSITIONS AND METHODS EMPLOYING N(6)-DISUBSTITUTED ADENOSINE COMPOUNDS

This application is a division of application Ser. No. 482,976, filed on June 25, 1974, and now U.S. Pat. No. 3,929,764.

The present invention relates to new N(6)-disubstituted adenosine compounds and to therapeutic compositions containing them.

The new N(6)-disubstituted adenosine compounds according to the present invention are compounds of the general formula:

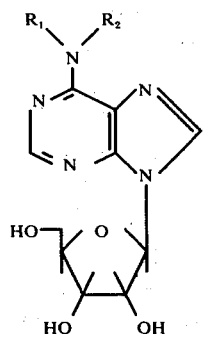

(I), wherein
$R_1$ is alkenyl, cycloalkenyl or cycloalkenyl-alkyl; and
$R_2$ is alkenyl, cycloalkenyl, straight or branched-chain alkyl, cycloalkyl, bicycloalkyl, alkyl-cycloalkyl, or alkyl-bicycloalkyl;
and the pharmacologically compatible salts thereof.

The alkyl and alkenyl radicals in the above-given general formula (I) can contain from 1 to 6 and preferably 1 to 4 carbon atoms and the cycloalkyl, cycloalkenyl or bicycloalkyl radical can contain from 5 to 10 carbon atoms.

We have, surprisingly, found that the compounds of general formula (I) do not possess the cardiac and circulatory action usual for adenosine derivatives but do exhibit an anti-lipolytic, anti-hyperlipaemic and anti-hypercholesterolaemic action. The new compounds according to the present invention bring about a considerable reduction of the concentration of free fatty acids, of triglycerides and of cholesterol in serum. Furthermore, a mild reduction of the blood sugar values is observed.

The new compounds according to the present invention can be prepared by reacting a purine riboside of the general formula:

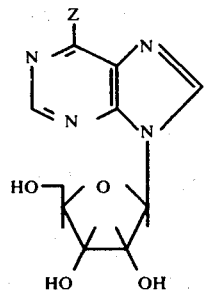

(II)

wherein Z is halogen, a reactive mercapto group of trimethylsilyloxy, with an amine of the general formula:

$R_1 - NH - R_2$  (III)

wherein $R_1$ and $R_2$ have the same meanings as above.

If desired, the hydroxyl groups of the ribose residue can be temporarily blocked by groups which can subsequently easily be split off. Furthermore, the compounds of general formula (I) obtained can, if desired, be subsequently converted into salts by reaction with acids.

For carrying out the reaction according to the present invention, a purine riboside (II) is reacted with an amine (III) in an inert solvent, for example, n-propanol, isopropanol, butanol, tetrahydrofuran or dioxan, preferably in the presence of a tertiary amine, for example, triethylamine, at ambient temperature or at a slightly elevated temperature.

The purine ribosides of general formula (II) used as starting materials, in which Z is a halogen atom, are described, for example, in Coll, Czech. Chem. Comm., 30, 1880/1965; compounds of general formula (II), in which Z is a mercapto group, are known from Chem. Pharm. Bull., 12, 951/1964; and compounds of general formula (II), in which Z is a trimethylsilyloxy radical, are described in Ang. Chem., 84, 347/1972.

When it is desired temporarily to block the hydroxyl groups of the ribose residue, there can be used the protective groups which are conventional in sugar chemistry. For this purpose, there can be used, for example, acyl radicals, preferably acetyl or benzoyl radicals, or ketals can be used, for example, the 2', 3'-isopropylidene compounds, which, after the condensation has taken place, can easily be converted into the free 2',3'-dihydroxy compounds by acid hydrolysis. On the other hand, when acyl radicals are used as protective groups, they can be split off by alkaline hydrolysis.

The pharmacologically compatible salts can be obtained in conventional manner by neutralization of the free bases (I) with non-toxic inorganic or organic acids, for example, hydrochloric acid, sulfuric acid, phosphoric acid, hydrobromic acid, acetic acid, lactic acid, citric acid, oxalic acid, malic acid, salicyclic acid, malonic acid or succinic acid.

The following examples illustrate the invention.

EXAMPLE 1

Preparation of N(6)-Methyl-N(6)-but-2-enyl-adenosine 7.3 g. triacetyl-6-chloro-9-($\beta$-D-ribofuranosyl)-purine, 2.1 g. methyl-but-2-enylamine and 2.8 ml. triethylamine were heated under reflux for 2 hours in 100 ml. isopropanol. After cooling, the reaction mixture was mixed with 200 ml. diethyl ether, extracted twice with water and the organic phase evaporated to dryness in a vacuum. The residue was dissolved in 100 ml. 25% methanolic ammonia and then left to stand overnight at ambient temperature. The solution was thereafter evaporated and the residue obtained was recrystallized from water. 4.1 g. (70% of theory) N(6)-methyl-N(6)-but-2-enyl-adenosine were obtained; m.p. 160° – 162° C.

The following compounds were obtained in an analogous manner from triacetyl-6-chloro-9-($\beta$-D-ribofuranosyl)-purine and a. N-methyl-cyclohex-3-enylamine:
N(6)-methyl-N(6)-cyclohex-3-enyl-adenosine; m.p. 120° – 122° C., yield 54% of theory;

b. diallylamine:

N(6)-diallyl-adenosine; m.p. 142°–144° C.; yield 85% of theory.

EXAMPLe 2

Preparation of N(6)-Methyl-N(6)-cyclohex-3-enylmethyl-adenosine 6.2 g. triacetyl-6-chloro-9-(β-D-ribofuranosyl)-purine, 2.5 g. methyl-cyclohex-3-enyl-methylamine and 2.8 ml. triethylamine were left to stand at ambient temperature for 16 hours in 100 ml. butanol. The reaction mixture was then mixed with 150 ml. diethyl ether, extracted twice with water and the organic phase evaporated to dryness in a vacuum. The residue was dissolved in 100 ml. 25% methanolic ammonia and left to stand for a few days at ambient temperature. 3.4 g. (60% of theory) N(6)-methyl-N(6)-cyclohex-3-enyl-methyl-adenosine crystallized out directly from the methanolic solution; m.p. 154°–156° C.

EXAMPLE 3

Preparation of N(6)-Allyl-N(6)-cyclohexyl-adenosine 10 g. triacetyl-6-chloro-9-(β-D-ribofuranosyl)-purine and 10 g. allyl-cyclohexylamine were heated under reflux for 1 hour in 100 ml. butanol. The butanol was then distilled off in a vacuum, the residue was dissolved in chloroform and the chloroform solution was then shaken out successively with dilute hydrochloric acid, dilute aqueous sodium bicarbonate solution and water. The chloroform solution was then dried over anhydrous sodium sulfate and evaporated to a syrup. This was dissolved in methanol and the solution, after the addition of 5 ml. 1N sodium methylate solution was heated for 10 minutes on a steambath. After cooling, the solution was distilled off to dryness, the residue was dissolved in chloroform and the chloroform solution was washed with water. The organic phase was dried and evaporated and the residue obtained recrystallized from ethanol. 6.1 g. (59% of theory) N(6)-allyl-N(6)-cyclohexyl-adenosine were obtained; m.p. 123° – 125° C.

The following compounds were obtained in an analogous manner from triacetyl-6-chloro-9-(β-D-ribofuranosyl)-purine and a. N-allyl-cyclopentylamine:
N(6)-allyl-N(6)-cyclopentyl-adenosine; m.p. 72°–74° C.; yield 46% of theory;

b. N-but-2-enyl-cyclohexylamine:
N(6)-but-2-N(6)-cyclohexyl-adenosine; m.p. 122°–114° C.; yield 59% of theory;

c. N-allyl-cycloheptylamine:
N(6)-allyl-N(6)-cycloheptyl-adenosine; m.p. 146°–148° C.; yield 40% of theory.

EXAMPLE 4

Preparation of N(6)-Cyclohexyl-N(6)-methallyl-adenosine 4.3 g. 6-chloro-9-(β-D-ribofuranosyl)-purine and 7.6 g. methallyl-cyclohexylamine were heated under reflux for 2 hours in 50 ml. butanol. The reaction mixture was evaporated in a vacuum and the residue obtained was dissolved in 50 ml. ethyl acetate and then extracted twice with 50 ml. amounts of water. The organic phase was dried, again evaporated and the residue recrystallized from methanol. 2.6 g. (43% of theory) N(6)-cyclohexyl-N(6)-methallyl-adenosine were obtained; m.p. 110°–112° C.

The following compounds were obtained in an analogous manner from 6-chloro-9-β-D-ribofuranosyl)-purine and a. N-methallyl-(4-methyl-cyclohexylamine):
N(6)-methyl-N(6)-(4-methyl-cyclohexyl)-adenosine; m.p. 124°–126° C.; yield 55% of theory;

b. dimethallylamine:
N(6)-dimethallyl-adenosine; m.p. 90 –93° C.; yield 48% of theory;

c. N-allyl-bicyclo[2,2,1]heptyl-(2)-amine:
N(6)-allyl-N(6)-bicyclo[2,2,1]heptyl-(2)-adenosine; m.p. 169°–171° C.; yield 46% of theory; and d. N-allyl-cyclohex-3-enylamine:
N(6)-allyl-N(6)-cyclohex-3-enyl-adenosine; m.p. 83°–86° C.; yield 42% of theory.

EXAMPLE 5

Preparation of N(6)-Cyclopentyl-N(6)-methallyl-adenosine 10.8 g. triacetyl-6-chloro-9-(β-D-ribofuranosyl)-purine and 10.5 g. cyclopentyl-methallylamine were heated under reflux for 2 hours in 100 ml. butanol. The solution was evaporated in a vacuum, the residue was taken up in chloroform and the chloroform phase was washed with dilute hydrochloric acid and water for the removal of excess amine. After drying over anhydrous sodium sulfate, the chloroform was distilled off and the remaining syrup was dissolved in methanol. After the addition of 5 ml. 1N sodium methylate solution, the solution was heated for a few minutes, treated with charcoal and cooled. After standing for a comparatively long period of time, 5.2 g. (53% of theory) N(6)-cyclopentyl-N(6)-methallyl-adenosine crystallized from the solution. After recrystallization from methanol, the compound melted at 105° – 107° C.

The following compounds were obtained in an analogous manner from triacetyl-6-chloro-9-(β-D-ribofuranosyl)-purine and a. N-methyl-methyllylamine:
N(6)-methallyl-N(6)-methyl-adenosine; m.p. 164°–166° C.; yield 54% of theory;

b. N-cycloheptyl-metallylamine:
N(6)-methallyl-N(6)-cycloheptyl-adenosine; m.p. 105°–107° C.; yield 62% of theory; and c. N-propyl-allylamine:
N(6)-allyl-N(6)-propyl-adenosine; m.p. 134°–136° C.; yield 29% of theory.

The compounds of this invention are, as indicated above, useful to decrease serum lipids in mammals. The effectiveness of the instant compounds on the lowering of triglycerides in the blood serum was determined following the procedure of Kreutz and Eggstein, modified by Schmidt et al (Z. klin Chem. u. klin, Biochem. 6, 1968, 156 –159). The procedure was carried out using for each compound 10 healthy male Sprague-Dawley rats, each weighing about 200 g. The animals were kept without food for 16 to 18 hours before application. The compounds were administered intraperitoneally (i.p.) in an aqueous buffered solution. The control group in each instance received only the solvent in the same manner of application. One hour after application of the compounds (or of the solvent alone for establishing the control values) the animals were killed and exsanguinated and in the obtained serum thereof the triglycerides determined enzymatically according to the method of Kreutz and Eggstein, modified by Schmidt et al, supra.

The results are set forth in the following Table 1, expressed as percentage reduction of the triglycerides in the serum of treated animals relative to the control animals.

TABLE 1

| Test Compound | Dosage(μg/kg) | Depression of serum triglycerides (in %) |
|---|---|---|
| N(6)-Allyl-N(6)-cyclohexyl-adenosine | 5 | 30 |
| N(6)-Allyl-N(6)-cyclopentyl-adenosine | 50 | 44 |
| N(6)-but-2-enyl-N(6)-cyclohexyl-adenosine | 25 | 30 |
| N(6)-Cyclohexyl-N(6)-methallyl-adenosine | 12.5 | 34 |
| N(6)-dimethallyl-adenosine | 50 | 37 |
| N(6)-allyl-N(6)-bicyclo[2,2,1]heptyl-(2)-adenosine | 50 | 63 |
| N(6)-allyl-N(6)-cyclohex-3-enyl-adenosine | 50 | 30 |
| N(6)-cyclopentyl-N(6)-methallyl-adenosine | 25 | 50 |
| nicotinic acid | 10.000 | 28 |

The data in Table 1 show a substantially better effectiveness of the new compounds as compared with nicotinic acid; even in a dosage which is 200 – 2000 fold of that of the new compounds, an identical effectiveness of the new compounds is not obtainable.

As previously indicated, the adenosine derivatives of this invention are readily adapted to therapeutic use as fat-affecting agents. The toxicity of the compounds of the invention has been found to be quite low or substantially non-existent when they are administered in amounts that are sufficient to achieve the desired therapeutic effect. Moreover, no other pharmacological side effects have been observed to occur as a result of their administration.

In accordance with the method of treatment of the present invention, the compounds can be given via the oral route. However, the compounds can also be administered as parenterals in the form of their solutions or suspensions. The compounds can be administered either alone and/or preferably in combination with a pharmaceutically acceptable carrier, and such administration can be carried out in both single and multiple dosages. More particularly, the compounds of this invention can be administered in a wide variety of different dosage forms wherein they are combined with various pharmaceutically acceptable inert carriers in the form of tablets, capsules, dragees, powders, aqueous suspensions, solutions, and the like. Such carriers include solid diluents or fillers, liquid aqueous media and various non-toxic organic solvents, etc. In general, the therapeutically effective compounds are present in such dosage forms at concentration levels ranging from about 0.01 to about 90% by weight of the total composition, i.e., in amounts which are sufficient to provide the desired unit dosage.

In dosage unit form, the compounds are set out herein are used in amounts of from 0.1 to 50 mg. active ingredient per dosage unit. Preferably, the compositions are compounded so that for parenteral administration, 0.5–5 mg. active compound/dosage unit is present and for oral administration 2–10 mg. of compound/dosage unit.

The present invention also provides new pharmaceutical compositions for oral or parenteral administration, containing at least one of the new compounds and/or at least one pharmacologically compatible salt thereof, in admixture with a solid or liquid pharmaceutical diluent or carrier. Examples of such forms of administration include tablets, capsules, dragees, syrups, solutions, suspensions, drops, suppositories and the like. For this purpose, the active material, admixed with a solid or liquid carrier, is brought into the desired form. Examples of solid carriers include lactose, mannitol, starch, talc, methyl cellulose, silicic acid, calcium phosphate, magnesium stearate, agar-agar and gelatine, to which, if desired, can be added flavoring and/or coloring materials. Liquid carrier materials for injection solutions must, of course, be sterile and are preferably placed into ampoules.

The precise dosages of compound to be administered to a given patient will depend on a number of factors, but generally a dosage in the range of 0.01 to 20 mg/kg per day will result in efficacious effects both by the oral and parenteral route, preferably of 0.5 to 5 mg/kg per day.

It will be understood that the specification and examples are illustrative but not limitative of the present invention and that other embodiments within the spirit and scope of the invention will suggest themselves to those skilled in the art.

What is claimed is:

1. Therapeutic composition for the treatment of excessively high fatty acid, triglyceride, or cholesterol contents in the serum of a mammal which composition comprises an effective amount of N(6)-disubstituted adenosine compound of the formula:

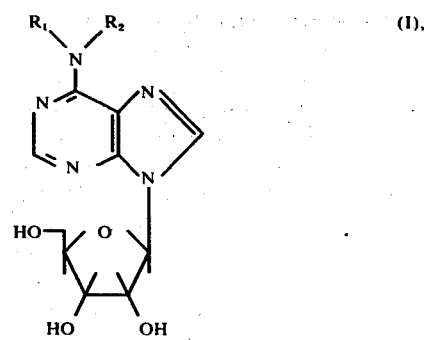

wherein
$R_1$ is alkenyl of up to 6 carbon atoms, cycloalkenyl or cycloalkenylalkyl of 5 to 10 carbon atoms in the cyclic moiety and up to 6 carbon atoms in the alkyl moiety; and
$R_2$ is alkenyl of up to 6 carbon atoms, cycloalkenyl of 5 to 10 carbon atoms, straight or branched-chain alkyl of up to 6 carbon atoms, cycloalkyl of 5 to 10 carbon atoms, bicycloalkyl of up to 10 carbon atoms, alkylcycloalkyl of from 5 to 10 carbon atoms in the cyclic moiety and up to 6 carbon atoms in the alkyl moiety; or alkyl-bicycloalkyl of up to 6 carbon atoms in the alkyl moiety and of up to 10 carbon atoms in the bicycloalkyl moiety; or a pharmacologically acceptable salt thereof and a pharmaceutically acceptable carrier.

2. Method for treating a mammal afflicted with too great a concentration of fatty acids, triglycerides or cholesterol in its serum which method comprises administering to such mammal effective amounts of an N(6)-disubstituted adenosine compound of the formula:

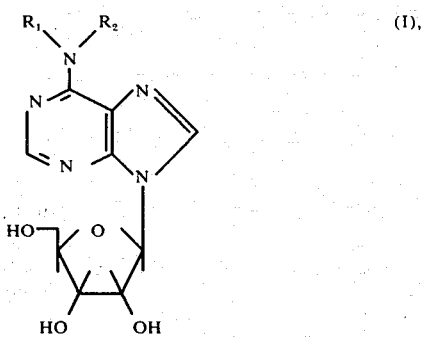

wherein
$R_1$ is alkenyl, of up to 6 carbon atoms, cycloalkenyl or cycloalkenylalkyl of 5 to 10 carbon atoms in the cyclic moiety and up to 6 carbon atoms in the alkyl moiety; and
$R_2$ is alkenyl of up to 6 carbon atoms, cycloalkenyl of 5 to 10 carbon atoms, straight or branched-chain alkyl of up to 6 carbon atoms, cycloalkyl of 5 to 10 carbon atoms, bicycloalkyl of up to 10 carbon atoms, alkylcycloalkyl of from 5 to 10 carbon atoms in the cyclic moiety and up to 6 carbon atoms in the alkyl moiety; or alkyl-bicycloalkyl of up to 6 carbon atoms in the alkyl moiety and of up to 10 carbon atoms in the bicycloalkyl moiety; or a pharmacologically acceptable salt thereof and a pharmaceutically acceptable carrier.

3. Method as claimed in claim 2 wherein said compound is selected from the group consisting of:
N(6)-allyl-N(6)-cyclohexyl-adenosine;
N(6)-but-2-enyl-N(6)-cyclohexyl-adenosine;
N(6)-cyclohexyl-N(6)-methallyl-adenosine;
N(6)-allyl-N(6)-bicyclo[2,2,1]heptyl-(2)-adenosine; and
N(6)cyclopentyl-N-(6)-methallyl-adenosine.

4. Method as claimed in claim 2 wherein said compound is administered at an average daily dose of 0.01 to 20 mg/kg per day.

5. Therapeutic composition as claimed in claim 1 wherein $R_1$ in said formula is alkenyl of up to 6 carbon atoms.

6. Therapeutic composition as claimed in claim 1 wherein $R_1$ in said formula is cycloalkenyl of from 5 to 10 carbon atoms.

7. Therapeutic composition as claimed in claim 1 wherein $R_1$ in said formula is cycloalkenyl-alkyl wherein the cycloalkenyl contains from 5 to 10 carbon atoms and the alkyl moiety contains from 1 to 6 carbon atoms.

8. Therapeutic composition as claimed in claim 1 wherein $R_2$ in said formula is alkenyl of up to 6 carbon atoms.

9. Therapeutic composition as claimed in claim 1 wherein $R_2$ in said formula is cycloalkenyl of from 5 to 10 carbon atoms.

10. Therapeutic composition as claimed in claim 1 wherein $R_2$ in said formula is alkyl of up to 6 carbon atoms.

11. Therapeutic composition as claimed in claim 1 wherein $R_2$ in said formula is cycloalkyl or alkylcycloalkyl wherein the cycloalkyl moiety contains from 5 to 10 carbon atoms and the alkyl moiety from 1 to 6 carbon atoms.

12. Therapeutic composition as claimed in claim 1 wherein $R_2$ in said formula is bicycloalkyl or alkyl substituted bicycloalkyl wherein the bicycloalkyl moiety contains from 5 to 10 carbon atoms and the alkyl moiety contains from 1 to 6 carbon atoms.

13. Therapeutic composition as claimed in claim 1 wherein said compound is designated N(6)-allyl-N(6)-cyclohexyl adenosine.

14. Therapeutic composition as claimed in claim 1 wherein said compound is designated N(6)-but-2-enyl-N(6)-cyclohexyl adenosine.

15. Therapeutic composition as claimed in claim 1 wherein said compound is designated N(6)-cyclohexyl-N(6)-methallyl-adenosine.

16. Therapeutic composition as claimed in claim 1 wherein said compound is designated N(6)-allyl-N(6)-bicyclo[2,2,1]-heptyl-(2)-adenosine.

17. Therapeutic composition as claimed in claim 1 wherein said compound is designated N(6)-cyclopentyl-N(6)-methallyl-adenosine.

18. Method as claimed in claim 2 wherein $R_1$ in said formula is alkenyl of up to 6 carbon atoms.

19. Method as claimed in claim 2 wherein $R_1$ in said formula is cycloalkenyl of from 5 to 10 carbon atoms.

20. Method as claimed in claim 2 wherein $R_1$ in said formula is cycloalkenyl-alkyl wherein the cycloalkenyl contains from 5 to 10 carbon atoms and the alkyl moiety contains from 1 to 6 carbon atoms.

21. Method as claimed in claim 2 wherein $R_2$ in said formula is alkenyl of up to 6 carbon atoms.

22. Method as claimed in claim 2 wherein $R_2$ in said formula is cycloalkenyl of from 5 to 10 carbon atoms.

23. Method as claimed in claim 2 wherein $R_2$ in said formula is alkyl of up to 6 carbon atoms.

24. Method as claimed in claim 2 wherein $R_2$ in said formula is cycloalkyl or alkylcycloalkyl wherein the cycloalkyl moiety contains from 5 to 10 carbon atoms and the alkyl moiety from 1 to 6 carbon atoms.

25. Method as claimed in claim 2 wherein $R_2$ in said formula is bicycloalkyl or alkyl substituted bicycloalkyl wherein the bicycloalkyl moiety contains from 5 to 10 carbon atoms and the alkyl moiety contains from 1 to 6 carbon atoms.

26. Method as claimed in claim 2 wherein said compound is designated N(6)-allyl-N(6)-cyclohexyl adenosine.

27. Method as claimed in claim 2 wherein said compound is designated N(6)-but-2-enyl-N(6)-cyclohexyl adenosine.

28. Method as claimed in claim 2 wherein said compound is designated N(6)-cyclohexyl-N-(6)-methallyl-adenosine.

29. Method as claimed in claim 2 wherein said compound is designated N(6)-allyl-N(6)-bicyclo-[2,2,1]-heptyl-(2)-adenosine.

30. Method as claimed in claim 2 wherein said compound is designated N(6)-cyclopentyl-N(6)-methallyl-adenosine.

* * * * *